(12) United States Patent
Hanson

(10) Patent No.: US 7,204,690 B2
(45) Date of Patent: *Apr. 17, 2007

(54) ORTHODONTIC DEVICES FOR USE WITH ARCH WIRES

(75) Inventor: G. Herbert Hanson, Hamilton (CA)

(73) Assignee: Augusta Developments Inc., Hamilton, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 11/484,578

(22) Filed: Jul. 12, 2006

(65) Prior Publication Data

US 2006/0252002 A1 Nov. 9, 2006

Related U.S. Application Data

(63) Continuation of application No. 10/623,528, filed on Jul. 22, 2003, now abandoned.

(51) Int. Cl.
*A61C 3/00* (2006.01)
(52) U.S. Cl. .......................... 433/10; 433/11
(58) Field of Classification Search ................ 433/10, 433/11, 13–14, 17
See application file for complete search history.

(56) References Cited

U.S. PATENT DOCUMENTS

| | | | | |
|---|---|---|---|---|
| 4,103,423 A | * | 8/1978 | Kessel | 433/10 |
| 4,698,017 A | * | 10/1987 | Hanson | 433/11 |
| 5,586,882 A | * | 12/1996 | Hanson | 433/13 |
| 5,685,711 A | * | 11/1997 | Hanson | 433/11 |
| 5,913,680 A | * | 6/1999 | Voudouris | 433/10 |
| 6,506,049 B2 | * | 1/2003 | Hanson | 433/11 |
| 6,659,767 B2 | * | 12/2003 | Abels et al. | 433/10 |
| 2002/0034715 A1 | * | 3/2002 | Hanson | 433/11 |

* cited by examiner

*Primary Examiner*—John J Wilson
(74) *Attorney, Agent, or Firm*—Stanley J. Rogers

(57) ABSTRACT

An orthodontic bracket or convertible buccal tube for use with arch wires has the usual mesial distal extending slot having one side open to receive the wire. The open side is closed by a shutter pivoting on a pivot pin, or coaxial pins, about a mesial distal axis, the shutter being latched in slot closed position to retain the arch wire in the slot. The device includes an attitude controlling spring member consisting of an integral extension of the part of the shutter member that closes the slot, the extension being thinner and therefore of greater flexibility than the relatively rigid shutter member. The extension can be progressively thinner that the shutter member from its junction therewith to a free end that engages the arch wire in the slot. In slot closed position a portion of the integral extension is positively engaged with a surface of the device body so as to preload the spring. Also in slot closed position the integral extension is engaged by lateral walls of the device body parallel to an occlusal, gingival, labial, lingual plane to protect it against mesial or distal directed stresses applied thereto.

11 Claims, 8 Drawing Sheets

ORTHODONTIC DEVICES FOR USE WITH ARCH WIRES

CROSS REFERENCE TO A RELATED APPLICATION

This application is a continuation of my prior application Ser. No. 10/623,528, filed 22 Jul., 2003, now abandoned, the priority of which is claimed under 35USC120.

FIELD OF THE INVENTION

This invention is concerned with improvements in or relating to orthodontic devices consisting of orthodontic brackets and convertible type tubes that are used in orthodontic procedures in cooperation with arch wires, and particularly such devices which have arch wire attitude controlling spring means as a permanent part thereof.

BACKGROUND OF THE INVENTION

Orthodontic procedures almost always employ a plurality of orthodontic brackets that are attached to respective teeth, usually by cementing them thereto, although in some circumstances the bracket may still be attached to a metal band which embraces the tooth. Each bracket has a mesial distal extending slot therein, usually of rectangular cross section in a gingival occlusal plane, and the brackets are connected together using an arch wire, so called because it is preformed to an optimum arch shape corresponding to the desired conformation of the teeth at the conclusion of the procedure. In the so-called labial procedures, which are the most commonly employed, the brackets are attached to the labial surfaces of the teeth and the slots open toward the labial for insertion and removal of the wire, which is retained in the slots by ligating means of some kind. In "lingual" procedures, which have the advantage that the brackets and the wire are usually concealed from frontal view, the brackets are attached to the lingual teeth surfaces and the slots open toward the lingual or occlusal. Arch wires of progressively increasing stiffness and, depending on the type of tooth movement to be achieved, also of different cross sections, are used one at a time. Historically, when first employed the brackets were "passive", in that ligation of the arch wire to the bracket to obtain the necessary action between them was external to the bracket, at first consisting of a soft metal wire twisted around them, while increasingly an elastomeric hoop or loop is used in place of wire.

The ends of the arch wire may be engaged in terminal tubes, usually attached to the molars so as to anchor the arch wire firmly in place. Tubes may also be employed on intermediate teeth in place of brackets whenever this is appropriate. In its simplest form a terminal or intermediate tube is passive and consists of a short piece of tube attached to a base by which it is mounted on the tooth surface, the tube bore opening at least mesially so that the arch wire end must be inserted therein. This is not always convenient, and may not be possible when the tube is on an intermediate tooth, and the solution is then to use a tube of the so-called convertible type, with which one side of the tube bore can be opened when required for insertion of the wire therein, or its removal. It is also possible to incorporate in such a tube an arch wire engaging attitude controlling spring member that will urge the wire into contact with two of the slot walls, whereupon the tube is active as well as convertible. It will be apparent from the foregoing brief description that there can be considerable overlap between the function and appearance of brackets and tubes, with the result that it may be possible for a particular orthodontic device to be considered by some orthodontists as a bracket, while others will think of it as a tube. In general, a device in which its body is noticeably bigger in gingival-occlusal dimension than mesially-distally will usually be regarded by most practitioners as a bracket, while one in which the opposite is the case will be regarded as a tube.

The term "orthodontic devices" as used herein, in both the specific description and in the claims, is intended therefore to include both brackets and convertible tubes within its scope. The adjective "buccal" commonly is used to indicate that a device is on teeth that are facing the cheeks, while "palatal" or "lingual" are used to indicate that a device is facing the palate and the tongue. More specifically palatal is used in referring to the "inward" facing surfaces of the upper bicuspids and molars, but increasingly lingual is used for all teeth, while labial is used to refer to the upper and lower canines and incisors, and buccal is used to refer to the upper and lower bicuspids and molars.

Brackets as used in the Hanson SPEED System (Trade Mark) are "active", sometimes referred to as "self-ligating", in that each comprises a permanent ligating spring member which embraces the bracket body and is moved thereon between slot open and slot closed positions, the spring member performing the dual functions of retaining the arch wire in the slot, and also urging it to an optimum position within the slot. Specific examples of such active brackets are disclosed and claimed in my U.S. Pat. Nos. 4,248,588 and 4,492,573.

In another line of development the orthodontic device is provided with a shutter which is movable between slot open and closed positions, in slot closed position retaining the arch wire in the slot. The shutter also functions, at least initially, by its engagement with the wire to urge the device and the arch wire to their optimum or neutral position relative to one another, at which position the constraint between them is minimized. Since in at least the initial stages of the procedure the arch wire will usually be of cross section smaller than the slot, such a device preferably is provided with an internal attitude controlling spring that protrudes into the slot to engage the wire and provide a desired controlling force. Such a shutter can be of thicker material than an embracing ligating spring so that it is relatively rigid and less flexible. It can therefore more easily be made much less sensitive to overstressing beyond the elastic limit of the material, while still being sufficiently flexible for it to be held securely in slot closed position by its jamming engagement with the device body while under the onerous conditions encountered in patients' mouths during typical orthodontic procedures. Examples of devices consisting of such brackets and convertible tubes are described and claimed in my U.S. Pat. No. 6,506,049, issued 14 Jan., 2003, the disclosure of which is incorporated herein by this reference.

There is a constant endeavor to provide devices that are as small and with as smooth an exterior as possible, for cosmetic reasons to please the patient, in order to reduce as much as possible any rough contact between the tongue, the devices and the adjacent mouth tissue with its consequent discomfort, and for hygienic reasons to reduce the number of areas in which food and dental plaque can accumulate. It is of interest to both orthodontists and patients to provide devices that interfere as little as possible with speech. The orthodontist is interested in addition to use devices that while low in cost provide fast, precise and effective movement and attitude control of the teeth.

There is increasing interest in the lingual technique, even though such procedures are more difficult to implement. A compromise is to use the lingual technique only for the upper arch, where the brackets and arch wire would otherwise be most visible, and the labial technique for the lower arch, where the brackets and arch wire are mostly hidden by the lower lip. Lingual and mixed lingual/labial procedures are of special interest to adult patients who are more concerned than children with appearance during the two to three year period required for a typical procedure. The compromise is not so suitable for older patients who tend to show their lower teeth more, and in some cases primarily display their lower anterior teeth. Small smooth devices are needed particularly for the lingual location because of ready access by the tongue, and the natural tendency for the tongue to explore any foreign object in the mouth. Attempts simply to reduce the size of existing devices are not generally successful, at least partly because changes in scale affects size parameters in different ratios, e.g. areas decrease in square ratio while volumes decrease in cube ratio, with the result that it becomes increasingly difficult, especially with the tiny spring members required, to find materials of the necessary properties. Examples of such small, smooth exterior brackets suitable for lingual procedures are those described and claimed in my U.S. Pat. Nos. 4,698,017 and 5,685,711, issued respectively 06 Oct. 1987 and 11 Nov. 1997

The manufacture of orthodontic devices and equipment is now a mature industry, and there is an ongoing requirement to provide devices that are efficient, economical and easy to use. Increasingly there is the added requirement for them to be as inexpensive as possible, especially if orthodontists are to be persuaded to make the changes in the procedures in which they were trained, and with which they are very familiar, and that the adoption of any new device usually entails.

SUMMARY OF THE INVENTION

It is a principal object of the invention therefore to provide new orthodontic devices, and particularly those which are of the type comprising a permanent attitude controlling metal spring that can engage an arch wire in the arch wire receiving slot.

It is another principal object to provide new devices of small size and of an exterior shape that makes them specially suitable for use in lingual techniques, particularly in association with incisor or canine teeth.

In accordance with the invention there is provided an orthodontic device for use with orthodontic arch wires comprising:
  a device body having labial, lingual, gingival, ocelusal, mesial and distal surface portions, the body having therein a mesial-distal extending arch wire receiving slot having one mesial distal extending side open to a device body surface portion to permit insertion of an arch wire into the slot and its removal therefrom:
  a pivot member mounted by the device body and establishing a mesial-distal extending pivot axis; and
  a shutter member mounted by the pivot member for pivoting movement about the pivot axis between a slot open position in which the open slot side is open, and a slot closed position in which the shutter member closes the open slot side to retain an arch wire in the slot;
  wherein the shutter member comprises:
    a pivot portion mounted by the pivot member for the pivoting movement of the shutter member; and
    a relatively rigid slot closure portion movable with the pivot portion, extending mesially distally with respect to the device body, and in the slot closure position closing the slot open side; and
    an attitude controlling spring member constituted by an integral extension of the slot closure portion further from the pivot portion and more flexible than the slot closure portion, the spring member being of recurved cross section in an occlusal, gingival, labial, lingual plane to have two arms, a first of which is integral with the slot closure portion and the second of which is integral with the first arm;
    wherein with the shutter member in slot closed position a free end portion of the second arm of the spring member extends into the arch wire receiving slot for engagement in a mesial-distal extending plane with an arch wire in the slot, such engagement urging the arch wire into engagement with the respective slot walls.

Preferably the integral extension spring member is progressively more flexible from the slot closure portion to the free end portion.

In the slot closed position a portion of the integral extension may be positively engaged with a surface of the device body so as to preload the integral portion and thereby urge the free end portion toward engagement with an arch wire in the arch wire slot, and also in this position the integral extension may be engaged by lateral walls of the device body parallel to an occlusal, gingival, labial, lingual plane to protect it against mesial or distal directed stresses applied thereto.

Devices of the invention may comprise latch means having latch members cooperating with one another and operative between the pivot member and the pivot portion when the shutter member is in slot closed position to retain the shutter member in that position.

DESCRIPTION OF THE DRAWINGS

Orthodontic devices that are particular preferred embodiments of the invention will now be described, by way of example with reference to the accompanying diagrammatic drawings wherein.

DESCRIPTION OF THE INVENTION

Figure 13:
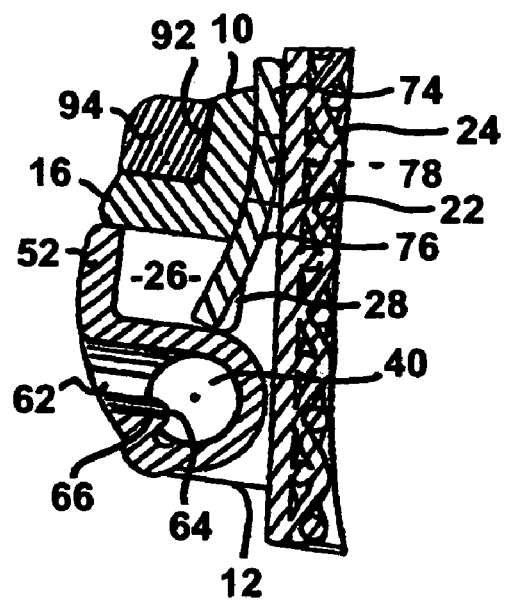
FIG. 13 (Sheet 5) is a central longitudinal cross section of a further embodiment, taken on the line 13—13 in FIG. 12, and showing one way in which the bracket can be provided with hooks for engagement with supplementary orthodontic devices.
Figure 12:
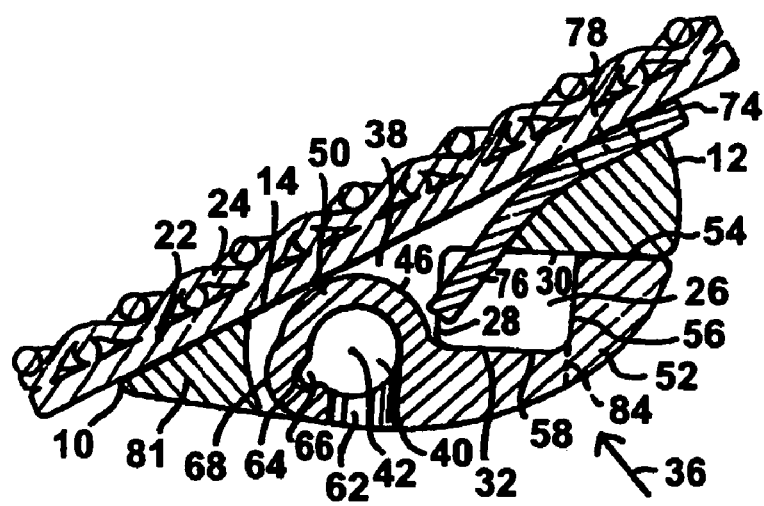
FIG. 12 (Sheet 5) is a central longitudinal cross section similar to FIGS. 10 and 11 of a further embodiment in which the placement of cooperating latch means members is reversed as compared with the other embodiments previously shown and described herein.
Figure 14:
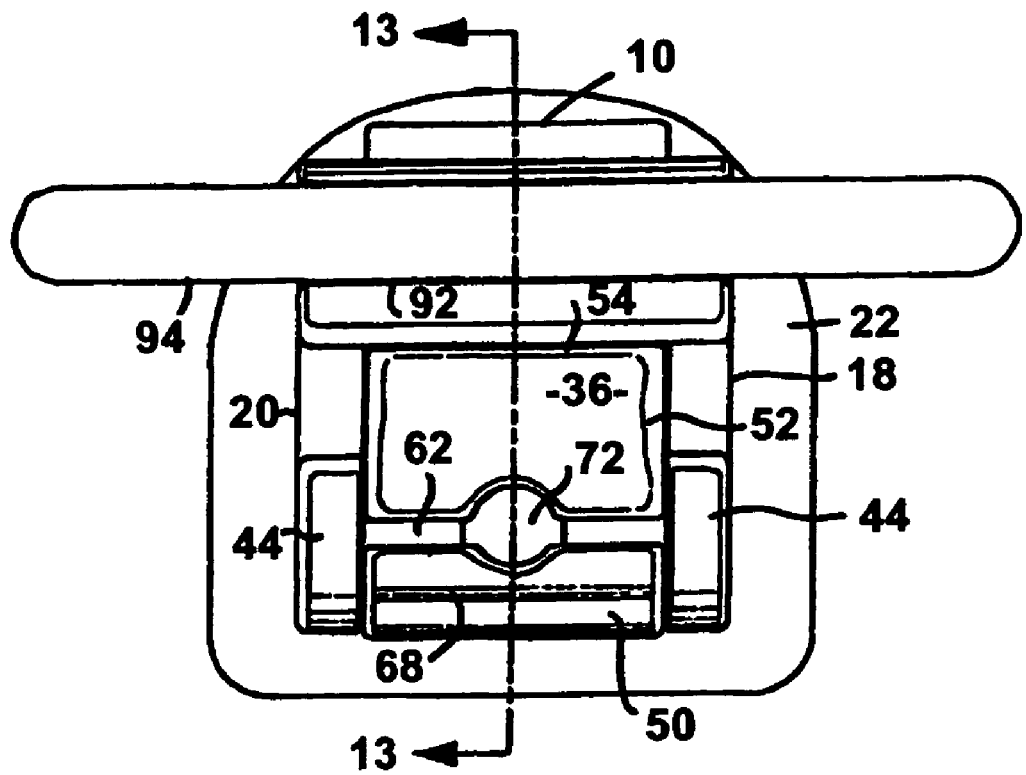
FIG. 14 is a view toward the labial of the embodiment of FIG. 13.

Similar parts are given the same reference number in all the Figures of the drawings wherever this is appropriate. It may be noted that the devices shown in FIGS. 1 through 11 are intended to be used attached to the lingual surfaces of incisor or canine teeth, while those shown in FIGS. 12–14 are intended to be used attached to the lingual surfaces of bicuspid or molar teeth.

In this specification and the appended claims, for convenience in language the devices and parts thereof are referred to, unless otherwise specified, as they would be used mounted in the upper arch region of a patient's mouth, especially since the brackets described are intended primarily for use in lingual procedures. However, all of the brackets of the invention may be used for either labial or lingual procedures. The labial and lingual direction designations are reversed between the two procedures, e.g. the bracket surface referred to as the labial surface in the labial procedure becomes the lingual surface in the lingual procedure, and vice versa, and the arch wire slot usually opens to the lingual and not the labial, although as described above it may instead open to the occlusal. Again for convenience in description the devices are described as having specific named surfaces but, as will be apparent, smooth exterior contours can only be achieved by avoiding sharp edges and sharp edged junctions wherever possible, and the various surfaces therefore usually merge smoothly with one another without a definite junction between them being apparent.

The devices described and shown herein are all intended for use in the so-called straight wire technique with which each bracket is attached to its respective tooth in an attitude such that, as the arch wire attempts to return to its preformed arch shape and to be straight as seen in a mesial-distal, labial-lingual plane, the tooth is moved toward its desired optimized position and attitude. In order for the arch wire to be straight at the conclusion of the procedure the brackets for different teeth must accommodate the very different inclinations of the tooth surfaces to which they are attached. There are two main methods by which this is done, either by suitable shaping of the bracket bases and of their base surfaces that contact the teeth surfaces, or by changing the inclination of the arch wire slots. In the brackets shown herein all of the torque requirements (rotation about a mesial distal axis), angulation requirements (rotation about a labial lingual axis), and first order pre-adjustments, are obtained by suitable shaping of the bracket bases, particularly of the surface that engages the tooth surface, and by variation of the base thickness, so that when the teeth are in their optimum attitude and rotational position all of the slot surfaces engaged by the arch wire are aligned. The other method of slot inclination can also be used in the brackets of the invention, either alone or in combination with the first-described method. However, when the other method is used, with some brackets the inclination of the slot may be so extreme that, for example, in a bracket fixed to the lingual surface of a central incisor no attempt is made to have the slot remain parallel with the labial lingual axis and instead, as mentioned above, it opens to the occlusal parallel to the gingival occlusal axis (as viewed from the mesial or distal). Such a configuration allows easier insertion of the arch wire into the lingually mounted brackets. Nevertheless such devices are within the scope of the language of the appended claims.

Figure 1:
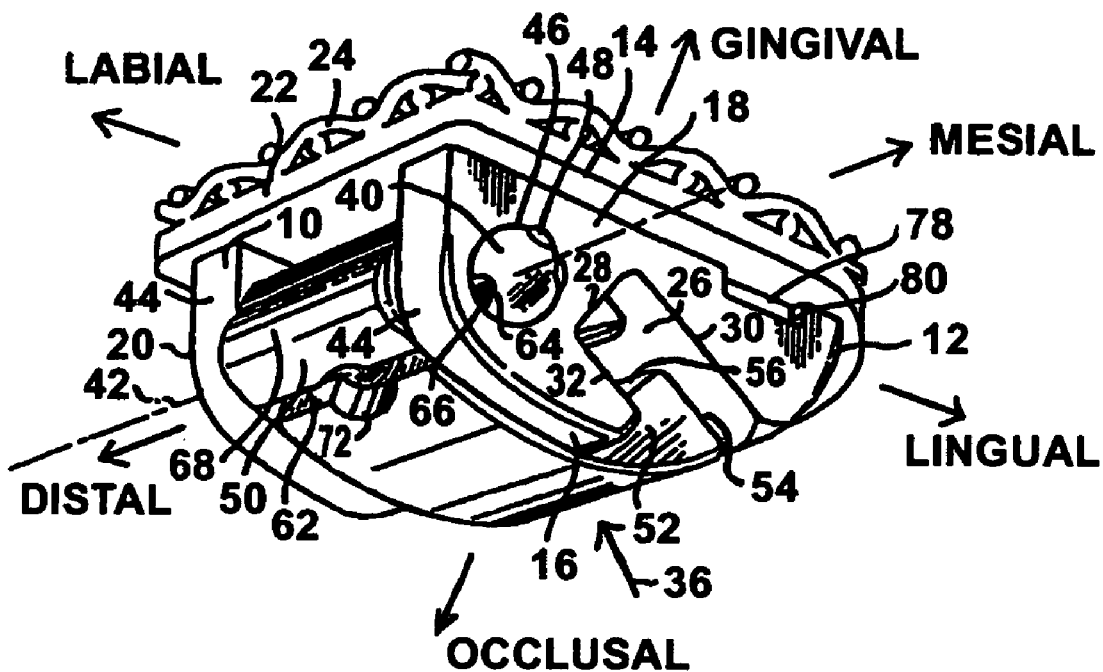
FIG. 1 is a perspective view from the mesial-occlusal of a first embodiment with its pivoting shutter member in slot closed position.
Figure 2:
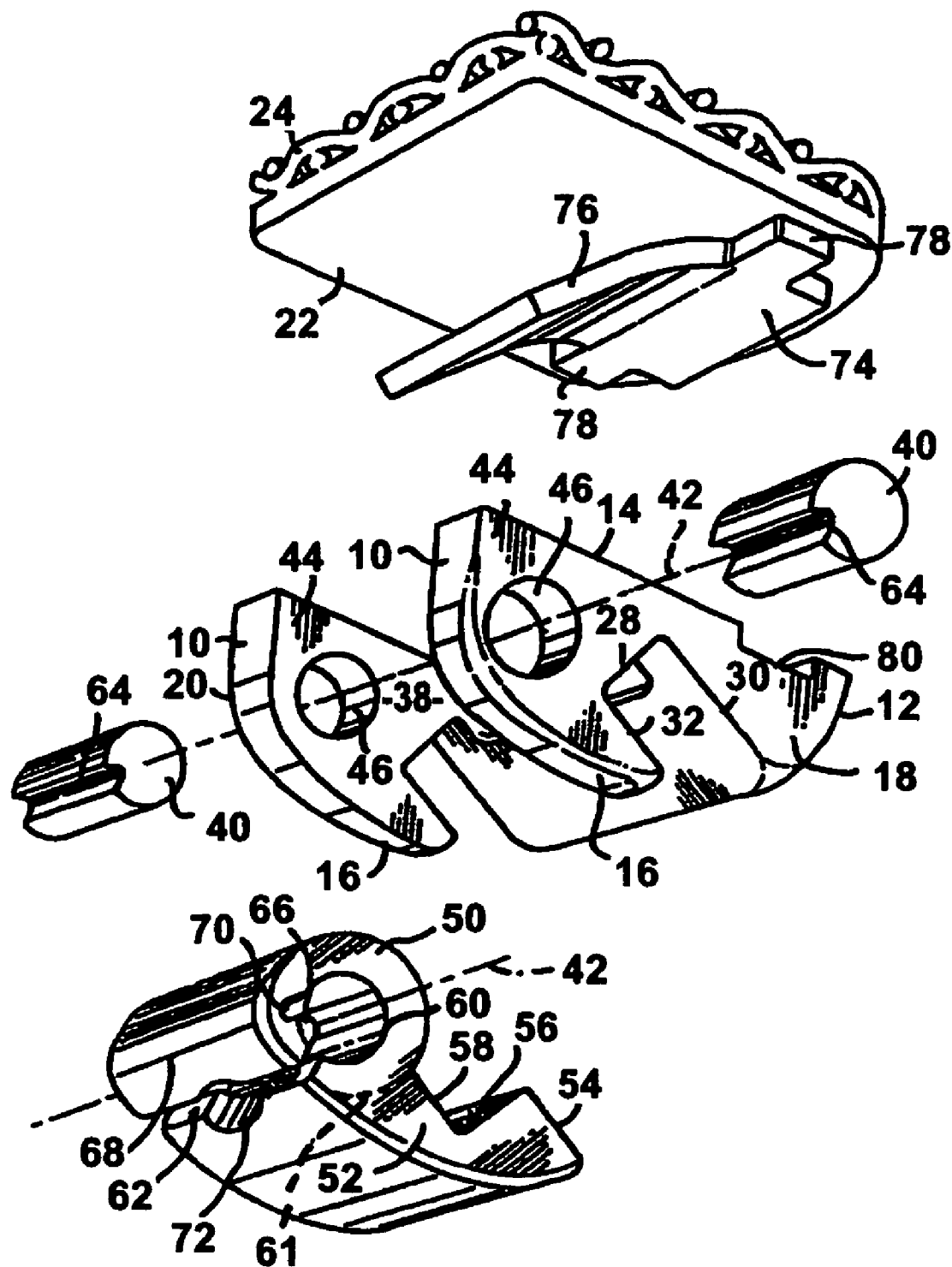
FIG. 2 is an exploded view from the same perspective as FIG. 1 of the first embodiment.

Referring now particularly to FIGS. 1 and 2, the bracket device shown therein consists of a bracket body comprising a bracket body member having labial, lingual, gingival, occlusal, mesial and distal surface portions 10, 12, 14, 16, 18 and 20 respectively, the orientation directions being shown in FIG. 1 by corresponding arrows. The bracket body member has attached to its gingival surface, as for example by laser welding along its edges, a bracket base 22 consisting of a thin metal foil, with a layer 24 of metal wire mesh attached to its gingival surface, the open pores of the mesh facilitating the cementing of the bracket to a tooth. All of the brackets shown and described herein are mounted on the respective tooth by such cementing, as increasingly is preferred, although they could also be mounted by the older method of attaching them to tooth-embracing bands, which method is not illustrated but is well known to those skilled in the art. The body member is provided with a mesial-distal extending arch wire receiving slot 26 having its lingual side open, the slot in this embodiment being of rectangular transverse cross section in a gingival-occlusal, labial-lingual plane and having labial, gingival and occlusal surfaces 28, 30 and 32 respectively. The slot receives an arch wire 34 (see for example FIGS. 10, 11, 16 and 17), which usually in the early stages of a procedure is of circular cross section and of small enough diameter for the bracket to slide freely along it once the arch wire is fully within the slot and fully aligned therein. Subsequently the arch wire usually is replaced by one of larger diameter, and thereafter with wires which also may instead be of D-shape or rectangular cross section.

Figure 3:
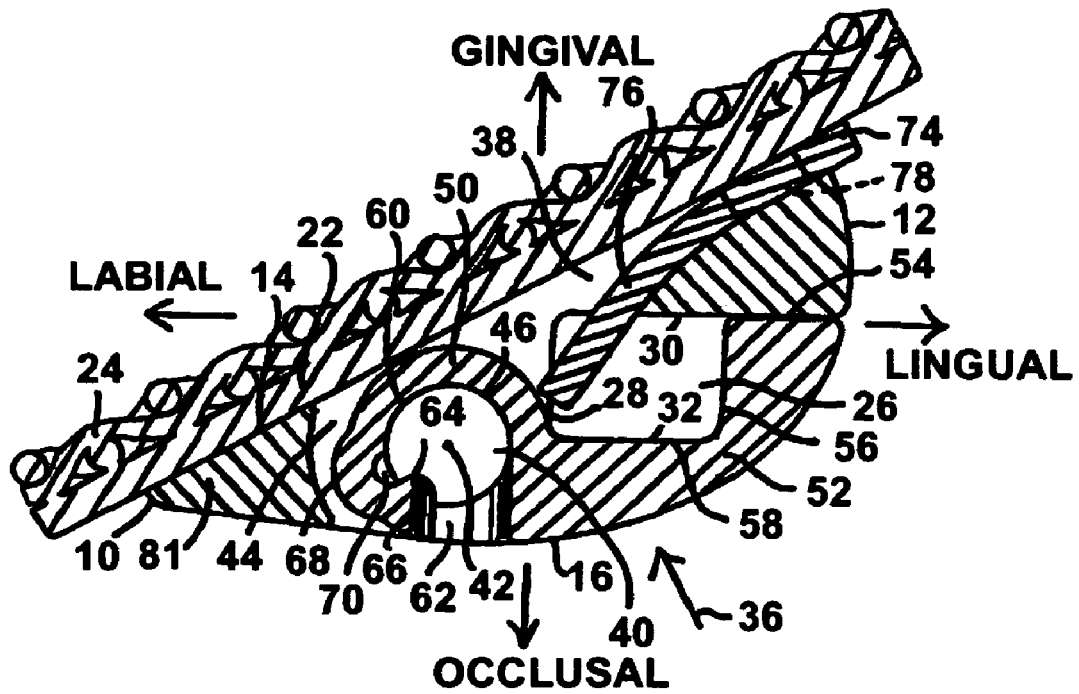
FIG. 3 is a longitudinal cross section in a central labial-lingual plane through a second embodiment with its shutter member in slot closed position.
Figure 4:
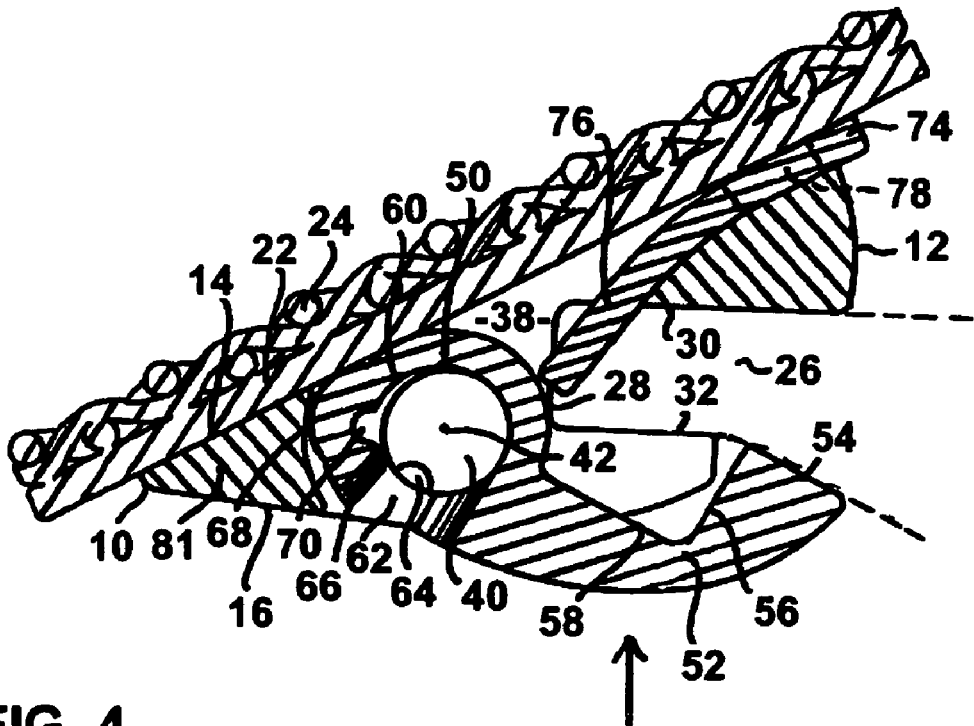
FIG. 4 is the same cross section as FIG. 3 of the second embodiment with the shutter member in slot open position.
Figure 5:
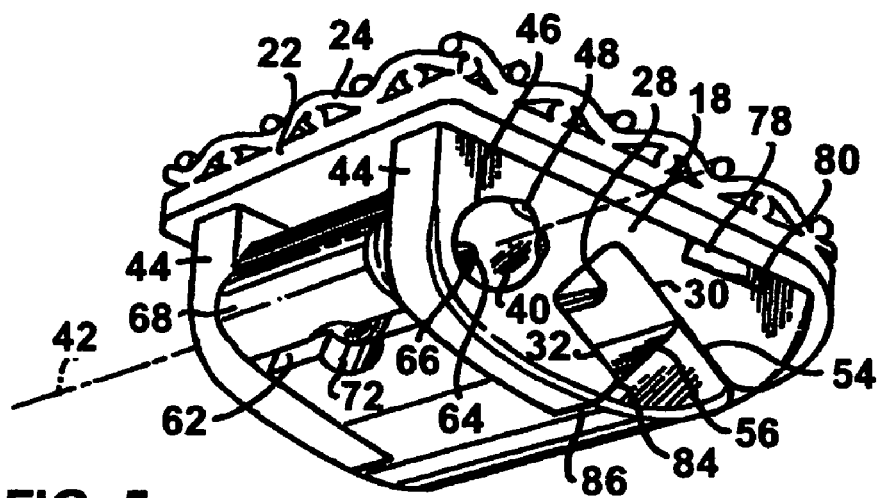
FIG. 5 is a perspective view similar to FIG. 1 of a further embodiment.
Figure 7:
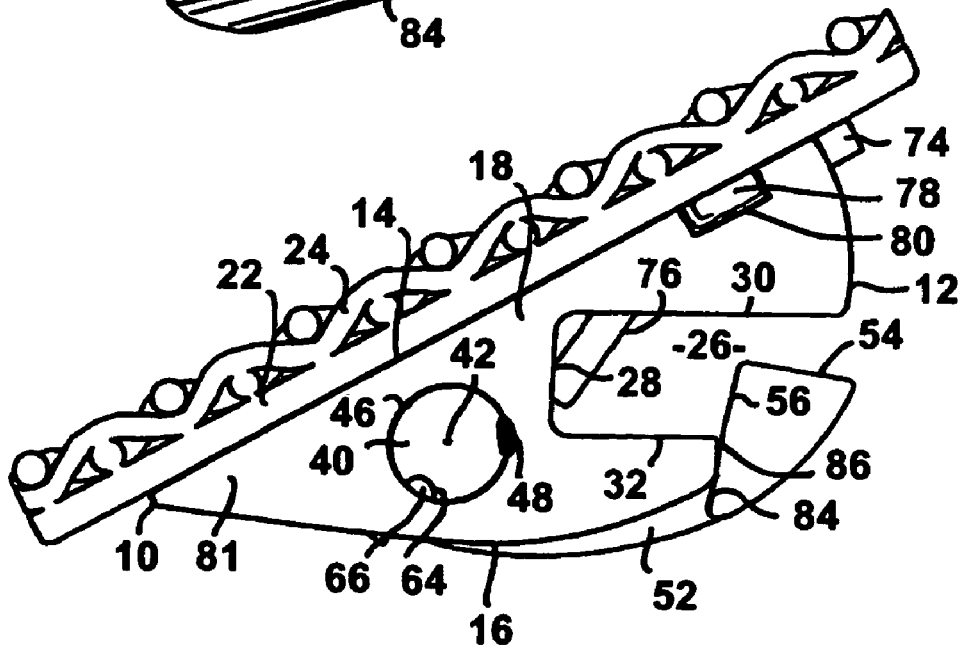
FIG. 7 is a side elevation from the mesial of a further embodiment that employs a shutter member of the same configuration as that in FIG. 6, and showing the start of jamming cooperation between the shutter member and the bracket body during movement of the shutter member toward slot closed position, such cooperation assisting in retaining the shutter member in that position.

Means for retaining the arch wire in the slot, and releasing it when required, consist of a shutter member, indicated generally by arrow 36, that is mounted by a pivot member in a centrally disposed recess 38 opening to the labial and occlusal surface portions 10 and 16. In this embodiment the pivot member consists of a pair of coaxial mesial-distal extending pivot pins 40 that pass through the shutter member and the bracket body, so that the member is movable about a common pivot axis 42 of the pins between a slot closed position, as shown in FIGS. 1 and 3, in which the shutter closes the open lingual slot side, and a slot open position, as shown in FIG. 4, in which the open lingual slot side is unobstructed. The facing ends of the pins are spaced from one another to provide a space between them whose function will be explained below. In this embodiment the pivot member is disposed in the body closer to the labial end than to the lingual end. The provision of the recess 38 in the bracket body member results in two parallel wing members 44 with parallel facing mesial and distal walls, the mesial-distal dimension between the two walls being such that the shutter member 36 has just enough clearance, but without any appreciable play, to move freely therein in its movement between slot open and closed positions. The pivot pins are of circular cross section and are engaged tightly in corresponding circular cross section bores 46 in the wing members; once engaged in these bores they are held rigidly against rotation, for example by laser spot welding their ends to the bracket body by spot welds 48, as shown in FIGS. 1, 5 and 7. The shutter member consists of a pivot portion 50 that is always within the recess 38, and through which the pivot pins 38 extend, and a slot closure portion 52, the latter being in this embodiment integral with the pivot portion, the shutter member having been machined from a single block of metal. The portion 52 is also sufficiently thick as to constitute a relatively rigid structure. In this embodiment the mesial-distal dimension of the slot closure portion is the same as that of the pivot portion. In the slot closed position of the shutter member surface 54 of the slot closure portion buts against archwire slot surface 30 to establish the fully closed position, while surface 56 doses the open lingual side of the arch wire slot, and surface 58 registers and aligns with slot surface 32 to form a continuation of that surface.

The shutter member is retained securely in the slot closed position by the interaction of latch means comprising cooperating latch members respectively with the pivot portion 50 and the pivot member pins 40. The pivot portion 50 has the form of a hollow cylindrical tube of at least approximately annular cross section in a gingival-occlusal plane that embraces the pivot pins 40, the tube being provided with a mesial-distal extending central bore 60 of diameter such that it is a close fit around the pins, while permitting the required pivoting rotation of the shutter member thereon. A mesial-distal, gingival-occlusal extending segment junction between the pivot and closure portions is indicated in FIG. 2 by a broken line 61. The pivot portion is provided close to this junction with a mesial-distal extending slot 62 that extends completely through its wall, so that the circular segment of the cylindrical tube wall that extends from the slot 62 to the junction 61 is able to move by flexing radially outward away from the pivot pins, such flexing being accompanied by a circumferential movement apart of the opposed facing walls of the slot. This movable segment of the pivot portion is made as long as possible to provide the maximum amount of flexing, and corresponding maximum amount of radially inward and outward movement of the free end of the segment. In practice the movable segment can constitute from about 200° to 270° of the total circumference of the pivot portion part wall.

In this embodiment the latch members provided by the latch means consist of mesial distal extending V or U transverse cross section latch grooves or recesses 64 in the surfaces of the pivot pins 40 and a mesial distal extending latch projection 66 of complementary profile immediately adjacent to the slot 62 and protruding radially inward from the inner wall of the bore 60. The relative positions of these latch members is such that in the slot closed position the projection is engaged snugly and securely in the grooves and positively retains the shutter member in that position. Movement of the shutter member out of that position requires that the movable segment be flexed radially outward against the resilience of the material of the member, and remain thus flexed while the shutter member is in any other position. The V or U cross sections of the recesses and projection provide a cam action in their engagement and disengagement. Such action is particularly advantageous during engagement in that as soon as the projection engages the downward inclined face of the recess the resilience of the movable segment positively moves the projection into full engagement in the recess with corresponding positive movement of the shutter member. Part 68 of the movable segment immediately adjacent to the projection 66 bulges radially outward, a groove 70 being provided in the inner wall of the pivot portion to maintain uniform wall thickness and to allow a cross section for the projection that ensures more secure engagement. The groove also ensures that there is no abrupt junction of the projection with the remainder of the moveable segment. As the shutter member rotates to move the slot closure portion away from the slot closed position the bulging part engages the adjacent wall of the base member 22, as shown in FIG. 4, thereby acting as a stop member preventing further rotation, so that the shutter member is held in a preferred slot open position in which the opposed closure member surface 52 and slot surface 30 provide an inwardly tapered opening that will facilitate capture of an arch wire and guide it into the slot 26.

The slot closure member is relatively easily moved from the slot open to slot closed position by finger pressure and/or by the pressure applied by a suitable dental tool. Opening is more difficult because of the smooth, flush outer surfaces and the projection 66 must be sprung from the grooves 64. The required opening movement is facilitated by the provision of a radially extending hole 72 in the centre of the slot 62, so that a dental tool 73 (see FIG. 8), such as a probe, can be inserted into the hole and used as a lever to rotate the shutter member, while at the same time assisting in the flexing of the movable segment by spreading the walls of the slot apart. As was described above, the two separate pivot pins 40 have their inner facing ends spaced apart, and the resultant space enables the tool to be inserted sufficiently deeply for adequate torque to be applied. The use of two separate pins does require accurate alignment of the two grooves 64 before the anchoring spot welds 46 are applied, and another method is to use a single grooved pivot pin and to drill the hole 72 after the pin is in welded in place, the hole then passing through the wall of the pivot portion and a sufficient depth into the pin (see FIG. 16). It will be noted that in slot closed position the occlusal surface of the slot closure portion 52 are flush with the corresponding occlusal surface 16 of the bracket body, and similarly the lingual surfaces of the slot closure portion is flush with the corresponding lingual surface 12 of the bracket body, so that in such position the bracket presents smooth, solid exterior surfaces that minimize the likelihood of rough contact between the brackets and the tongue and adjacent tissue of the mouth.

The bracket as so far described is "passive", in that the only control of tooth movement provided is by the interaction produced by contact between the arch wire and the walls of the arch wire slot 26. It is preferred in most procedures that the brackets be "active", i.e. that they include some inherent means for controlling the attitude of the bracket relative to the arch wire, and to that end each is provided within the recess 38 with a thin sheet metal flat attitude controlling spring member. The spring member has a fixed end portion 74 that is held rigidly in the bracket body, and a free end portion 76 extending into the arch wire receiving slot for engagement in a mesial-distal, labial-lingual plane with an arch wire in the slot, such engagement urging the arch wire toward the cooperating surfaces of the arch wire slot and the slot closure portion. The spring is of vertical cross shape in plan (St. George orientation) with transversely extending side arms 78, and may be inserted in the bracket as it is assembled with the side arms sandwiched between the bracket body member and the base member 22, recesses 80 being provided in the body member to receive the side arms. Other methods of attachment can be employed such as laser welding or riveting.

The force with which the spring engages an arch wire is dependent primarily on the dimensions of the spring, particularly its width and thickness, and also upon the cross section dimension of the arch wire. The force can also be adjusted by forming the spring with different amounts of preloading before the bracket is assembled, for example by adjustment of its profile. A preferred material for the springs and shutter members used in the orthodontic devices of the invention is the family of nickel-titanium alloys, commonly referred to as superelastic shape recovery metal alloys, in that they can withstand without damage strains of as high as about 6–8%, as compared to the usual maximum of about 0.5% for stainless steels, the materials most commonly previously used. There is now adequate literature available as to the performance and fabrication of springs using these materials and further explanation is not required herein. Stainless steels of the required qualities will usually continue to be the material of choice for the device body and the pivot pins.

Referring now particularly to FIGS. 3 and 4, in this embodiment the function and operation of the shutter member 36 and its latch means, and of the attitude controlling spring 74-78, are identical to the same elements in the embodiment of FIGS. 1 and 2. The principal difference is that the shutter member receiving recess 38 now opens only to the body occlusal surface, instead of to both the labial and occlusal surfaces, and the body extends much further toward the labial beyond the pivot pins (or pivot pin if a single pin is used) to provide a solid wedge shaped body portion 81 that reduces (tapers) in gingival occlusal dimension toward the labial, the labial surface 10 being almost non-existent. The occlusal surface of this body portion 81 is a smooth extension of the occlusal surface 16 of the remainder of the body. The arch wire slot 26 still opens to the lingual surface.

Canine and incisor teeth are characterized in that their labial-lingual dimension decreases progressively from the gingival to the occlusal, as contrasted with bicuspids and molars which are more nearly uniform in dimensions in this direction. A common problem encountered in orthodontic treatment is that the patient has a deep-bite malocclusion in which the lower incisors are set too far lingually from the upper incisors for the teeth to meet properly when the jaw is closed, so that the bite is deeper than it should be. Brackets of the invention, as illustrated by FIGS. 3 and 4, are particularly suited for use when treating such a problem in that the gingival-occlusal dimension of the bracket body can readily be made to decrease progressively from the lingual to the labial, and this decrease can be made to correspond approximately to the average increase in dimension of a canine or incisor tooth. With such a bracket attached to such a lingual surface the labial-lingual dimension of the bracket-tooth combination is at least approximately uniform from the occlusal to the gingival, so that the bracket occlusal surface lies in a mesial-distal, labial-lingual extending plane. This, together with the fact that in the slot closed position the occlusal surface portion of the shutter member 36 is flush with the occlusal surface portion 16 of the bracket body, means that the bracket is thereby able to provide a combined occlusal surface which is unobstructed and can constitute a bite plane against which the cutting edge of the respective opposed lower tooth can engage during biting action. Once the malocclusion has been corrected the lower incisor no longer engages the opposed lingual mounted bracket. This structure therefore has a number of practical advantages. The added labial extension adds structural strength and can with advantage be made somewhat longer than is shown. The lingual brackets now also function as bite planes to prevent the lower incisors from reaching their usual deep-bite malocclusion over-closure, and can therefore replace the acrylic bite plates that are placed in the mouth to correct this. They also operate similarly to prevent any interference with the brackets on the lower teeth while the malocclusion is present, so that they can be bonded to the teeth without fear that they will be detached as a result of over-biting. It also permits the posterior teeth to be erupted during the procedure to further reduce the overbite. Such brackets are described and claimed in my U.S. Pat. No. 6,506,049, issued 14 Jan., 2003, referred to above.

A bracket as illustrated by FIGS. 5 through 8 differs from those of FIGS. 1 through 4 in that the part of the slot closure portion 52 providing the slot closure surface 56 is wider in the mesial-distal direction than the pivot portion 50, and preferably its width is that of the body member, so that its end surfaces 82 are flush with the mesial and distal surfaces 18 and 20 of the body member. The extended slot closure portion therefore provides mesial and distal extending surfaces 84 that are extensions of the surfaces 56, and that are able to cooperate with surfaces 86 on the bracket body wings 44 in providing an additional restraining force that assists the latch means in retaining the shutter member in the slot closed position. Thus, the dimensions of the bracket body and of the shutter member are such that, as the shutter member moves about the pivot axis 42 toward the slot closed position, the surfaces 84 at first engage and then rub tightly against the corresponding surfaces 86 with an interference fit. Owing to their very small dimensions there may be a very small amount of flexing of the parts 82 toward the lingual against the elasticity of the material. Once in the slot closed position the moving interference fit engagement between the surfaces becomes a stationary butting interference fit engagement, with the butting sections of the shutter member permanently very slightly flexed lingually outward from the bracket body to provide a correspondingly directed retaining force. Owing to this tight rubbing engagement an increased, but entirely acceptable, amount of force is required to move the shutter member into the slot closed position until the latch means engage, and similarly an increased amount of force is required to disengage the latch means and move the shutter member toward the slot open position. The extended slot closure surfaces also are operative to provide the bracket with increased rotational control during the orthodontic procedure because of the increased length of mesial distal engagement with the arch wire.

Such a method of adding to the retention the slot closure member in slot closed position is completely feasible with a product such as an orthodontic bracket in that the number of openings and closings it is likely to experience during its working life is limited, so that the possibility of wear of the rubbing engaging surfaces is minimal. Orthodontic brackets are already of necessity manufactured to very close tolerances (e.g. 0.00025 mm or 0.0001 in) so that the required jamming interference fit can easily be achieved. The tiny amount of any deflection produced in the end portions 82 is highly unlikely to even approach the yield point of the material, so that permanent deflection is correspondingly highly unlikely. In the event that in some brackets of a batch the amount of this retaining force is considered to be insufficient this can be corrected by the application of a very thin (e.g. 0.0025 mm or 0.001 in) hard adherent coating to one or both of the engaging jamming surfaces 84 and 86.

Figure 8:
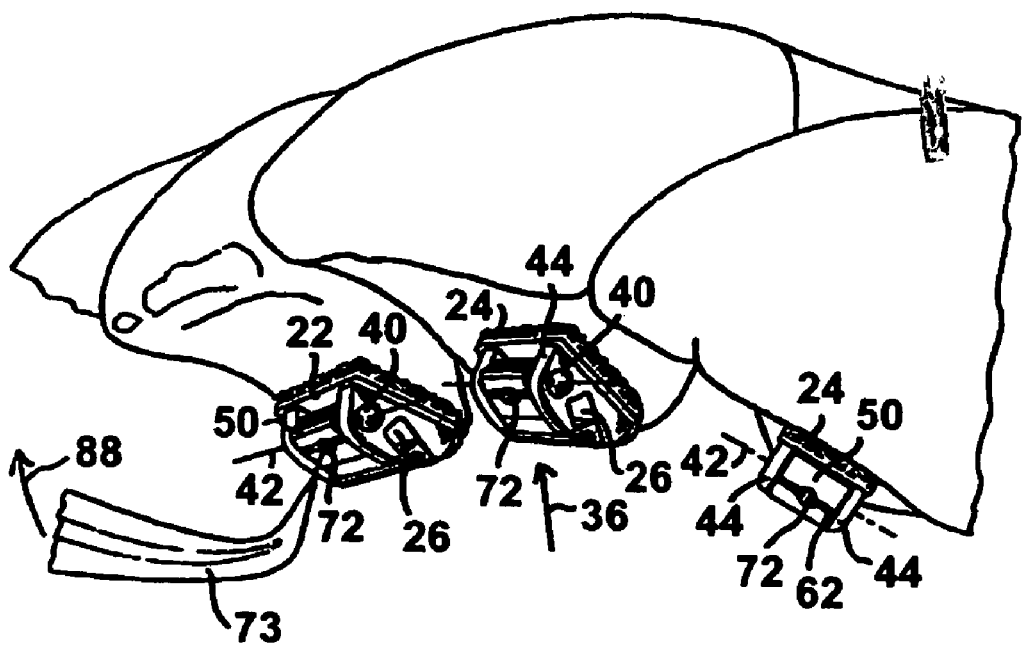
FIG. 8 (Sheet 1) is a perspective view showing brackets as shown in FIG. 5 attached to the lingual surfaces of incisor teeth, and showing also a tool suitable for moving the shutter member to slot open position.
Figure 6:
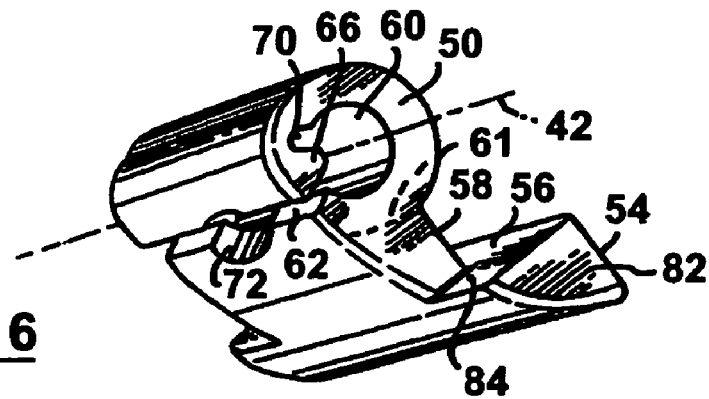
FIG. 6 is a perspective view from the same perspective as FIG. 5, but showing only the shutter member of the embodiment of FIG. 5.
Figure 9:
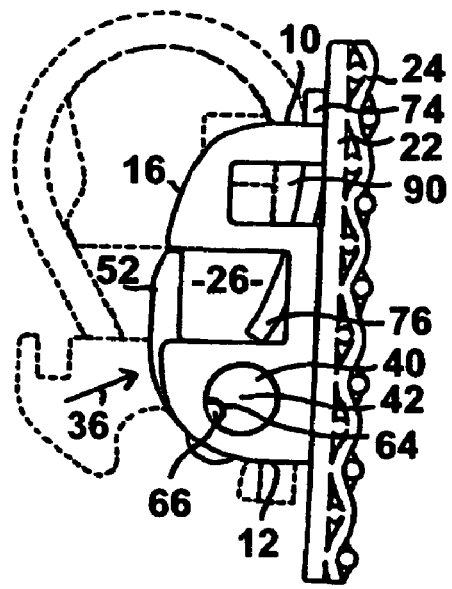
FIG. 9 is a side elevation from the mesial showing a bracket of the invention in solid lines, and one of my prior art brackets in broken lines, the outlines of the brackets being superimposed upon one another so as to provide a comparison of their sizes.

FIG. 8 is a perspective view showing brackets of the invention, of the kind illustrated by FIGS. 5 and 6, cemented to the lingual surfaces of adult upper incisors in order to show the extremely small size that is possible. For example only, brackets of the invention can readily be produced having a mesial distal dimension (not including the base 22 or mesh 24) of 1.96 mm (0.077 in) to 2.5 mm (0.098 in), a labial lingual dimension of 1.2 mm (0.048 in), and a gingival occlusal dimension of 1.8 mm (0.070 in) to 3.05 mm (0.112 in). Again for example only, in brackets of such dimensions the pivot pin/s 40 typically will be of diameter in the range 0.4 mm (0.016 in) to 0.5 mm (0.020 in), preferably 0.45 mm (0.018 in), while the latch groove 64 and the latch projection 66 will be of radial dimension in the range 0.05 mm (0.002 in) to 0.10 mm (0.004 in), preferably 0.062 mm (0.0025 in). The figure also shows a typical dental tool 73 that can be used in moving the shutter member from closed to open position by inserting it into the hole 72 and rotating it in the direction of arrow 88. FIG. 9 shows a bracket of the invention attached to a base 22, and to the same scale a prior art Hanson SPEED system (Trademark) bracket as disclosed for example in my prior U.S. Pat. No. 4,492,573, referred to above, the outlines of the two brackets being superimposed in order to demonstrate clearly the difference in their sizes and the small dimensions to which it is possible to make the new brackets.

Figure 10:
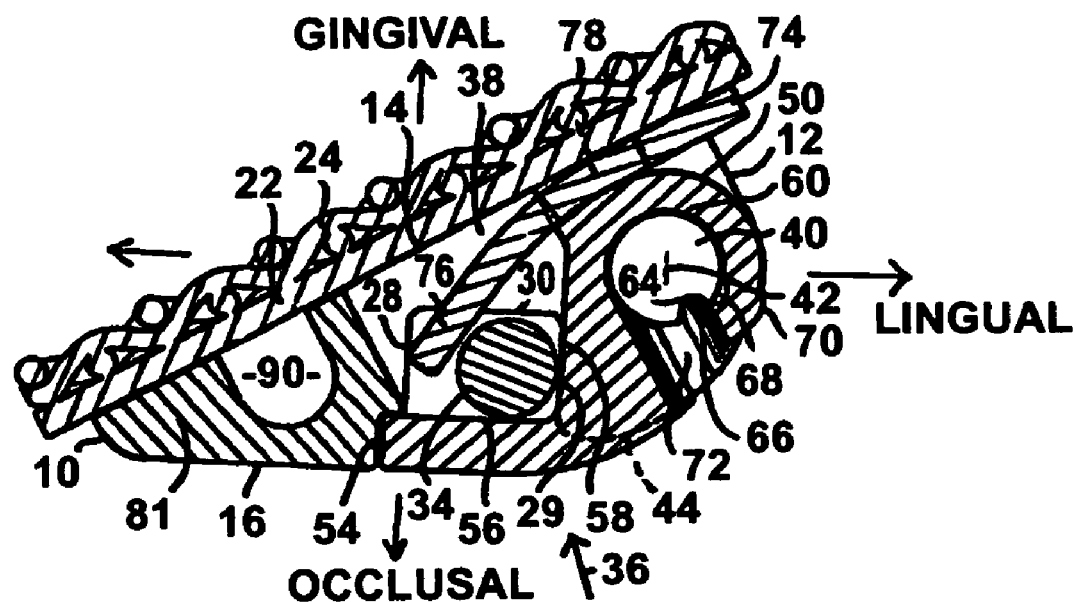
FIGS. 10 and 11 (sheet 6) are central longitudinal cross sections similar to FIGS. 3 and 4 of a further embodiment, in which the shutter member is positioned toward the lingual end of the bracket body, instead of toward the labial end.
Figure 11:
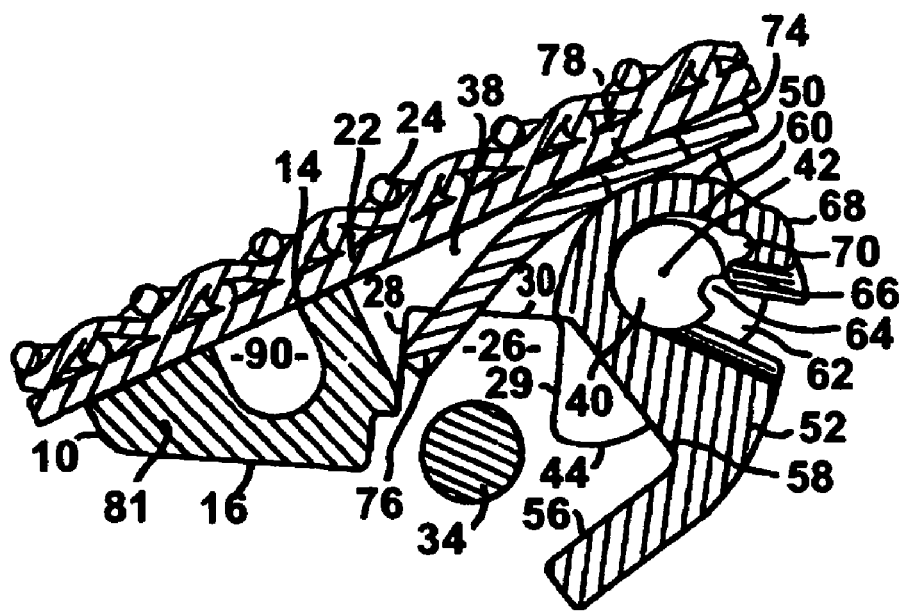

FIGS. 10 and 11 are central longitudinal cross sections through a further embodiment in which the shutter member 36 is disposed adjacent to the lingual end of the bracket body rather than to the labial end, such a bracket being appropriate for use on the lingual surfaces of upper incisors and canines. FIG. 10 shows the shutter member in the slot closed position and with a round cross section arch wire 34 in the slot 26. In this embodiment the attitude controlling spring 74-78 is sandwiched between the base member 22 and the movable pivot portion 50 of the shutter member, the part thereof which buts against the spring being of uniform radius about the axis 42 until the bulge 70 engages the spring to act as a stop member for the shutter member in slot open position. This configuration enables the bracket body to be provided toward its labial end with a mesial distal extending bore 90 that can receive a supplementary wire, or used as an anchor point for other supplementary orthodontic devices.

The bracket of FIG. 12 is intended for application to canine and incisor teeth, but the variation in structure which this illustrates is equally applicable to those intended for application to molar or bicuspid teeth. The function and operation of the shutter member 36, its latch means, and the attitude controlling spring 74-78, are the same. The structural difference is that the disposition of the latch means members, namely the latch grooves or recesses 64 and the latch projection 66, is reversed. A mesial distal extending recess 64 is provided in the wall of pivot portion 50, while a cooperating radial outward extending projection 66 is provided on the pivot pin or pins 40. The movable segment of the wall carries the recess 64 as close as possible to its free end to provide the maximum length of wall that is flexed radially outward in order to disengage the latch means.

Referring now to FIGS. 13 (sheet 5) and 14 (sheet 7), brackets as illustrated thereby can be attached to the teeth lingual surfaces and can also be attached to the labial surfaces of all teeth if given the appropriate built in torque and provided with base members 22 ("stand offs") of appropriate shape and dimensions. Brackets frequently are provided with attachment means for auxiliary devices consisting of quite large external hooks and mushroom headed receptors for anchors and tension devices and, particularly with devices intended for lingual procedures, these are likely to cause problems owing to their engagement with the adjacent mouth surfaces and the tongue. Owing to the extremely small size of the brackets of the invention it becomes more difficult to provide such attachment means in a single machining process, and this may be done in two stages by providing a shallow mesial distal extending recess 92 at the junction of the lingual and gingival surface portions, and then soldering or brazing into the slot a short piece 94 of arch wire of appropriate cross section of mesial distal length such that its ends protrude beyond the mesial and distal surfaces of the bracket body.

Figure 15:
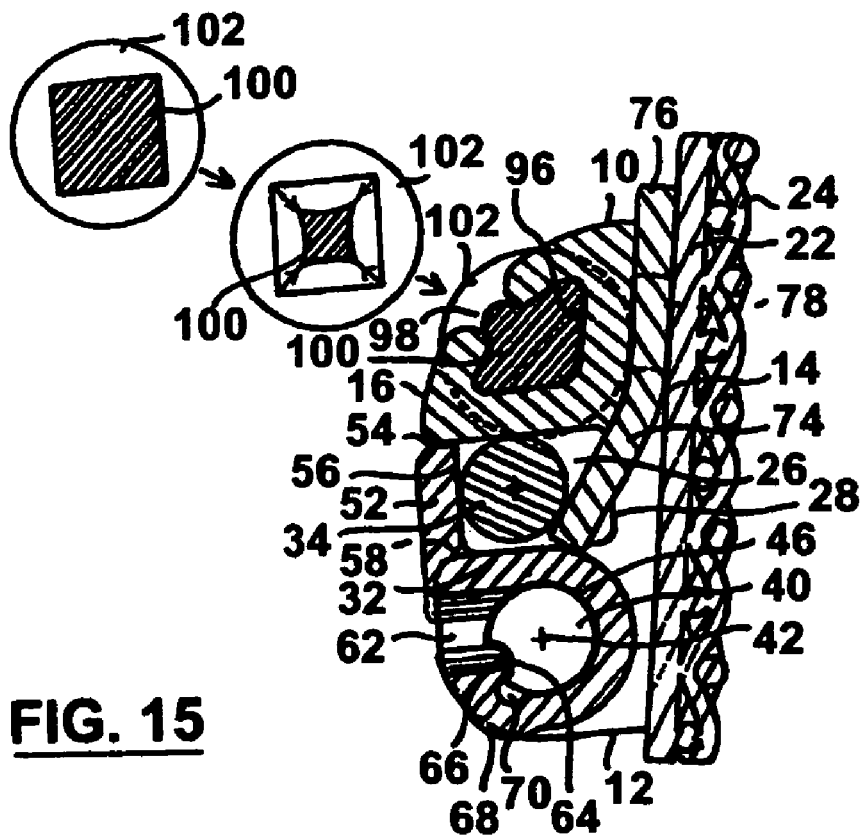
FIG. 15 is a central longitudinal cross section of a further embodiment provided with a mesial distal extending additional open-mouthed slot in which elastomeric threads can be engaged.

FIG. 15 shows a further embodiment in which the bracket is provided with means that permit ready attachment thereto of an auxiliary element, such as an elastomeric thread. The bracket body is provided approximately at the junction of the lingual and gingival surfaces with a mesial distal extending slot 96 having a narrow mesial distal extending mouth 98 through which an elastomeric thread 100 can be squeezed. This is done by stretching the thread longitudinally until its cross section has been reduced from its normal relaxed or somewhat tensed outline, as shown at the upper left of the Figure, to a much reduced highly stretched outline, as shown in the middle of the Figure. Once inside the slot and allowed to return to its normal outline, as shown in the right hand part of the Figure, and as permitted by the cross section shape of the slot, it will frictionally oppose movement of the ribbon through the slot, or can be knotted or otherwise provided with an enlarged stop member 102 to prevent mesial or distal movement through the slot or escape therefrom in those directions. For example, mesial or distal directed tension can be applied to the bracket by use of a thread provided at regular intervals along its length with stop knots or beads 102 of a size that cannot pass through the slot. The tension can be adjusted by cutting an appropriate length of the thread and engaging it in the slot with the endmost knot or bead butting against the appropriate mesial or distal surface.

Figure 16:
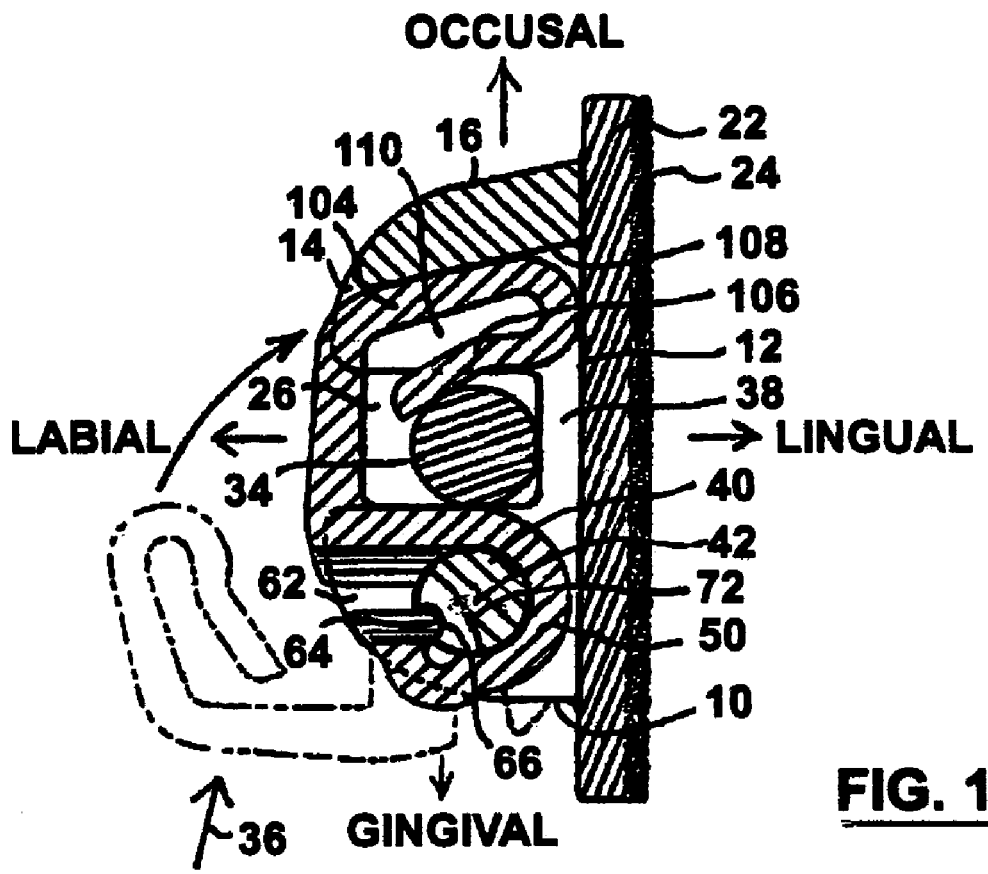
FIGS. 16 and 17 are central longitudinal cross sections of respective further embodiments in which an attitude controlling spring member to render the bracket active is provided by an integral more flexible extension of the shutter member.

The bracket of FIG. 16 is intended for use on lower central incisors in labial procedures, its arch wire slot 26 opening to the labial, while the shutter member 36 is pivotally mounted about a pivot axis 42 closer to the gingival end. The device differs in structure from those described above in that an integral attitude controlling spring member is constituted by an integral portion 104, 106 of the shutter member that is an extension of the slot closure portion 52 and is thinner than the slot closure portion so as to be more flexible than the relatively rigid slot closure portion. This extension is of recurved cross section in an occlusal, gingival, labial, lingual plane and consists of two somewhat approximately parallel arms 104 and 106, thus extending the effective length of the spring and providing greater opportunity for decreasing its thickness and thereby increasing its flexibility. The arm 104 is an integral extension of the slot closure portion, while the arm 106 constitutes a spring member free end portion that in slot closed position extends into the slot for engagement in a mesial-distal extending plane with an arch wire 34 in the slot, such engagement urging the arch wire into engagement with lingual and gingival slot surfaces 29 and 30 respectively. The recurved structure also facilitates the required positioning of the free end for the required engagement with the arch wire. In this embodiment, as is shown in the Figure, the integral extension is made progressively thinner along its length from its integral junction with the shutter portion to the end of the free end portion, with corresponding progressive increase in flexibility and to minimize the possibility of the generation of stress zones, such as could be caused by an abrupt change in thickness. The arm 106 is therefore somewhat more flexible than the arm 104.

In the slot closed position a part of the flexible portion, and in this embodiment more specifically the occlusal facing surface of the arm 104, which is relatively straight, is positively engaged along most of its length with an inclined gingivally facing surface 108 of the device body so as preload the flexible portion and urge the free end portion toward engagement with the arch wire. This inclined surface and the preload that it provides also facilitate the retention of the shutter member in slot closed position, since the spring member must be flexed toward the gingival in order to move from that position. The flexible portion is of mesial distal dimension to be a close fit within the device body recess 38, so that in slot closed position it is engaged by the mesial and distal facing lateral wall surfaces 110 of the device body, parallel to the occlusal-gingival-labial-lingual plane, to protect it against displacement under mesial or distal directed stresses applied thereto. In this embodiment the cement-receiving layer 24 of metal wire mesh is replaced with a thin layer of sintered metal powder. Such a structure makes full use of the much higher strain-tolerant characteristics of the nickel-titanium alloys referred to above, and these are the preferred materials for the manufacture of the combined shutter member and attitude controlling spring.

Figure 17:
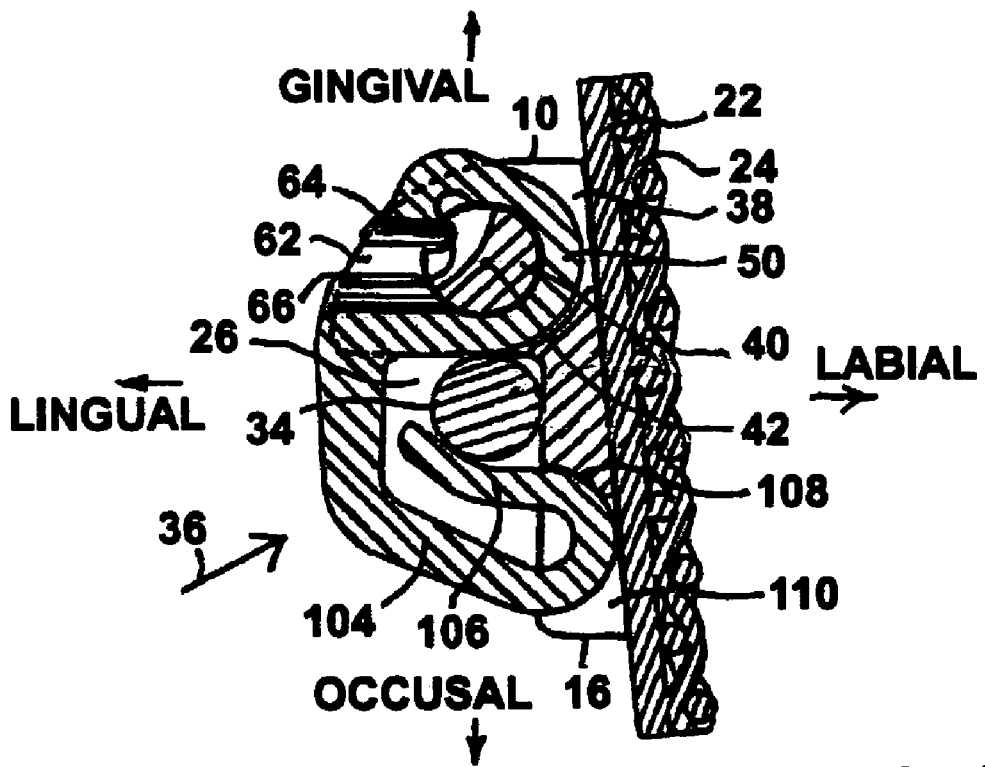

The device of FIG. 17 is for use on upper bicuspids and has its arch wire slot opening to the occusal; otherwise the device functions in the same manner as that of FIG. 16, the spring member constituted by the more flexible integral extension also, as shown in the Figure, being of progressively less thickness along its length from the junction with the shutter portion to its free end. The surface 108 which is engaged to provide preload for the spring member is of much shorter length and engages the arm 106 very close to its junction with the arm 104, the surface being curved to be of complementary shape. The supporting surfaces 110 are of much shorter labial-lingual length, but are adequate to protect the spring member against mesial-distal directed forces, even though they engage only the curved junction between the two arms. In both of the two last described embodiments the latch means constituted by the latch groove 64 and cooperating latch projection 66 can be replaced by an equivalent latch means, for example as shown in my prior U.S. Pat. No. 5,224,858, the disclosure of which is incorporated herein by this reference.

LIST OF REFERENCE SIGNS

10. Bracket body labial surface portion
12 Bracket body lingual surface portion
14 Bracket body gingival surface portion
16 Bracket body occlusal surface portion
18 Bracket body mesial surface portion
20 Bracket body distal surface portion
22 Bracket body base foil
24 Metal wire mesh
26 Arch wire receiving slot
28 Slot labial surface
29 Slot lingual surface (when slot opens to the occlusal)
30 Slot gingival surface
32 Slot occlusal surface
34 Arch wire
36 Shutter member
38 Bracket body recess
40 Pivot member (pins) for shutter member
42 Pivot pin pivot axis
44 Bracket body wing members
46 Pivot pin receiving bores in wing members 44
48 Spot welds holding pivot member stationary
50 Shutter member (36) pivot portion
52 Shutter member (36) slot closure portion
54 Slot closure portion surface butting arch wire slot surface 30
56 Slot closure portion surface closing labial or occlusal side of arch wire slot
58 Slot closure portion surface aligning with arch wire slot surface 32
60 Bore in pivot portion receiving pivot member
61 Junction between pivot and slot closure portions of shutter member 36
62 Through slot in wall of pivot portion 50
64 Latch grooves in pivot pins 40 or in pivot portion 50
66 Latch projection on pivot portion 50 or on pivot member 40
68 Bulged part of movable segment constituting stop member
70 Groove on opposite wall of bulged part
72 Radially extending tool receiving hole
73 Tool for moving shutter member from slot closed position
74 Fixed end portion of attitude controlling spring
76 Free end portion of attitude controlling spring
78 Attitude controlling spring side arms
80 Recesses in bracket body receiving spring side arms 78
81 Wedge shaped body part providing extended bite plane
82 End surfaces of mesial-distal extending slot closure portion
84 Extended slot closure surfaces of slot closure portion
86 Surfaces on bracket body wings 44 cooperating with surfaces 84
88 Arrow showing operative direction of rotation of tool 71
90 Supplementary mesial distal extending bore in bracket body
92 Mesial distal extending recess receiving hook forming wire 94
94 Wire in recess 92 forming external hooks
96 Mesial distal slot receiving elastomeric ribbons
98 Narrow mouth of slot 96
100 Elastomeric thread
102 Stop bead or knot on elastomeric thread
104 Arm of recurved spring extension attached to shutter member
106 Arm of recurved spring extension providing free end
108 Surface of device body engaged by arm 106 to provide preload
110 Mesial distal device body surfaces supporting spring extension 104/106
111 Recess in body receiving shutter member edge
112 End stop member crimped on to arch wire cable 34

I claim:

1. An orthodontic device for use with orthodontic arch wires comprising:

a device body having labial, lingual, gingival, occlusal, mesial and distal surface portions, the body having therein a mesial-distal extending arch wire receiving slot having one mesial distal extending side open to a device body surface portion to permit insertion of an arch wire into the slot and its removal therefrom;

a pivot member mounted by the device body and establishing a mesial-distal extending pivot axis; and a shutter member mounted by the pivot member for pivoting movement about the pivot axis between a slot open position in which the open slot side is open, and a slot closed position in which the shutter member closes the open slot side to retain an arch wire in the slot;

wherein the shutter member comprises;

a pivot portion mounted by the pivot member for the pivoting movement of the shutter member; and a relatively rigid slot closure portion movable with the pivot portion, extending mesially distally with respect to the device body, and in the slot closure position closing the slot open side; and an attitude controlling spring member constituted by an integral extension of the slot closure portion further from the pivot portion and more flexible than the slot closure portion, the integral extension spring member being of recurved cross section in an occlusal, gingival, labial, lingual plane to have two arms, a first of which is integral with the slot closure portion and the second of which is integral with the first arm;

wherein with the shutter member in slot closed position a free end portion of the second arm of the spring member extends into the arch wire receiving slot for engagement in a mesial-distal extending plane with an arch wire in the slot, such engagement urging the arch wire into engagement with the respective slot walls.

2. An orthodontic device as claimed in claim 1, wherein the integral extension spring member is progressively more flexible from the slot closure portion to the free end portion.

3. An orthodontic device as claimed in claim 2, wherein in the slot closed position a portion of the integral extension is positively engaged with a surface of the device body so as to preload the integral portion and thereby urge the free end portion toward engagement with an arch wire in the arch wire slot.

4. An orthodontic device as claimed in claim 2, wherein in slot closed position the integral extension is engaged by lateral walls of the device body parallel to an occlusal, gingival, lingual plane to protect it against mesial or distal directed stresses applied thereto.

5. An orthodontic device as claimed in claim 2, end including latch means having latch members cooperating with one another and operative between the pivot member and the pivot portion when the shutter member is in slot closed position to retain the shutter member in that position.

6. An orthodontic device as claimed in claim 1, wherein in the slot closed position a portion of the integral extension is positively engaged with a surface of the device body so as to preload the integral portion and thereby urge the free end portion toward engagement with an arch wire in the arch wire slot.

7. An orthodontic device as claimed in claim 6, wherein in slot closed position the integral extension is engaged by lateral walls of the device body parallel to an ocolusal, gingival, labial, lingual plane to protect it against mesial or distal directed stresses applied thereto.

8. An orthodontic device as claimed in claim 6, and including latch means having latch members cooperating with one another and operative between the pivot member and the pivot portion when the shutter member is in slot closed position to retain the shutter member in that position.

9. An orthodontic device as claimed in claim 1, wherein in slot closed position the integral extension is engaged by lateral walls of the device body parallel to an occlusal, gingival, labial, lingual plane to protect it against mesial or distal directed stresses applied thereto.

10. An orthodontic device as claimed in claim 9, and including latch means having latch members cooperating with one another and operative between the pivot member and the pivot portion when the shutter member is in slot closed position to retain the shutter member in that position.

11. An orthodontic device as claimed in claim 1, and including latch means having latch members cooperating with one another and operative between the pivot member and the pivot portion when the shutter member is in slot closed position to retain the shutter member in that position.

* * * * *